US006706045B2

United States Patent
Lin et al.

(10) Patent No.: US 6,706,045 B2
(45) Date of Patent: Mar. 16, 2004

(54) CLAMPING CONNECTOR FOR SPINAL FIXATION SYSTEMS

(75) Inventors: Chih-I Lin, Diamond Bar, CA (US); David Nichols, Memphis, TN (US)

(73) Assignee: Howmedica Osteonics Corp., Allendale, NJ (US)

( * ) Notice: Subject to any disclaimer, the term of this patent is extended or adjusted under 35 U.S.C. 154(b) by 0 days.

(21) Appl. No.: 10/159,235

(22) Filed: May 31, 2002

(65) Prior Publication Data

US 2002/0143332 A1 Oct. 3, 2002

Related U.S. Application Data

(63) Continuation of application No. 08/857,137, filed on May 15, 1997, now Pat. No. 6,413,257.

(51) Int. Cl.$^7$ ............................................. A61B 17/70
(52) U.S. Cl. ........................................... 606/61; 606/73
(58) Field of Search ............................. 606/54, 59, 60, 606/61, 72, 73

(56) References Cited

U.S. PATENT DOCUMENTS

| 4,269,178 A | 5/1981 | Keene |
| 4,641,636 A | 2/1987 | Cotrel |
| 4,815,453 A | 3/1989 | Cotrel |
| 4,887,596 A | 12/1989 | Sherman |
| 4,987,892 A | 1/1991 | Krag et al. |
| 5,002,542 A | 3/1991 | Frigg |
| 5,010,879 A | 4/1991 | Moriya et al. |
| 5,074,864 A | 12/1991 | Cozad et al. |
| 5,102,412 A | 4/1992 | Rogozinski |
| 5,112,332 A | 5/1992 | Cozad et al. |
| 5,116,334 A | 5/1992 | Cozad et al. |
| 5,122,131 A | 6/1992 | Tsou |
| 5,129,900 A | 7/1992 | Asher et al. |
| 5,176,680 A | 1/1993 | Vignaud et al. |
| 5,181,917 A | 1/1993 | Rogozinski |
| 5,209,752 A | 5/1993 | Ashman et al. |

(List continued on next page.)

FOREIGN PATENT DOCUMENTS

| CA | 2215485 | 9/1996 |
| CA | 2206853 | 12/1997 |
| EP | 0553042 A1 | 1/1993 |
| EP | 0 553 424 A1 * | 8/1993 |
| EP | 0811357 | 8/1997 |
| FR | 2730155 A | 7/1993 |
| WO | WO 95/26687 | 10/1995 |

Primary Examiner—David O. Reip
(74) Attorney, Agent, or Firm—Lerner, David, Littenberg, Krumholz & Mentlik, LLP

(57) ABSTRACT

The present invention is directed to one piece connector for connecting angularly misaligned implanted pedicle screws to transverse spinal rods in spinal fixation systems. The body portion includes a bore having an inside diameter and a longitudinal axis, with the longitudinal axis of the bore being positioned perpendicular to the longitudinal axis of the leg portion. The leg portion includes a slot placed through a section of the leg portion, along the transverse axis of the leg portion and parallel to the longitudinal axis of the leg portion. The slot intersects the bore of the body portion perpendicular to the longitudinal axis of the bore. The slot allows the one piece connector to be securely clamped around a longitudinal spinal rod when a pedicle screw is implanted at variable distances from the longitudinal spinal rod. The one piece connector allows for angular misalignment of an implanted pedicle screw in relation to a longitudinal spinal rod and the one piece connector, and for the attachment of the one piece connector to both the longitudinal spinal rod and to the implanted pedicle screw with a single locking mechanism when the one piece connector is used in a spinal fixation system.

21 Claims, 3 Drawing Sheets

U.S. PATENT DOCUMENTS

| | | |
|---|---|---|
| 5,217,497 A | 6/1993 | Mehdian |
| 5,222,954 A | 6/1993 | Baker et al. |
| 5,254,118 A | 10/1993 | Mirkovic |
| 5,257,993 A | 11/1993 | Asher et al. |
| 5,261,909 A | 11/1993 | Sutterlin et al. |
| 5,261,912 A | 11/1993 | Frigg |
| 5,281,222 A | 1/1994 | Allard et al. |
| 5,282,801 A | 2/1994 | Sherman |
| 5,282,862 A | 2/1994 | Baker et al. |
| 5,312,404 A | 5/1994 | Asher et al. |
| 5,330,473 A | 7/1994 | Howland |
| 5,344,422 A | 9/1994 | Frigg |
| 5,346,493 A | 9/1994 | Stahurski et al. |
| 5,368,594 A | 11/1994 | Martin et al. |
| 5,380,323 A | 1/1995 | Howland |
| 5,380,326 A | 1/1995 | Lin |
| 5,385,583 A | 1/1995 | Cotrel |
| 5,437,669 A | 8/1995 | Yuan et al. |
| 5,437,671 A | 8/1995 | Lozier et al. |
| 5,474,551 A | 12/1995 | Finn et al. |
| 5,476,462 A | 12/1995 | Allard et al. |
| 5,478,340 A | 12/1995 | Kluger |
| 5,498,262 A | 3/1996 | Bryan |
| 5,507,746 A | 4/1996 | Lin |
| 5,527,314 A | 6/1996 | Brumfield et al. |
| 5,562,663 A | 10/1996 | Wisnewski et al. |
| 5,562,666 A | 10/1996 | Brumfield et al. |
| 5,582,612 A | 12/1996 | Lin |
| 5,591,165 A | 1/1997 | Jackson |
| 5,609,592 A | 3/1997 | Brumfield et al. |
| 5,611,800 A | 3/1997 | Davis et al. |
| 5,613,968 A | 3/1997 | Lin |
| 5,630,817 A | 5/1997 | Rokegem et al. |
| 5,634,925 A | 6/1997 | Urbanski |

* cited by examiner

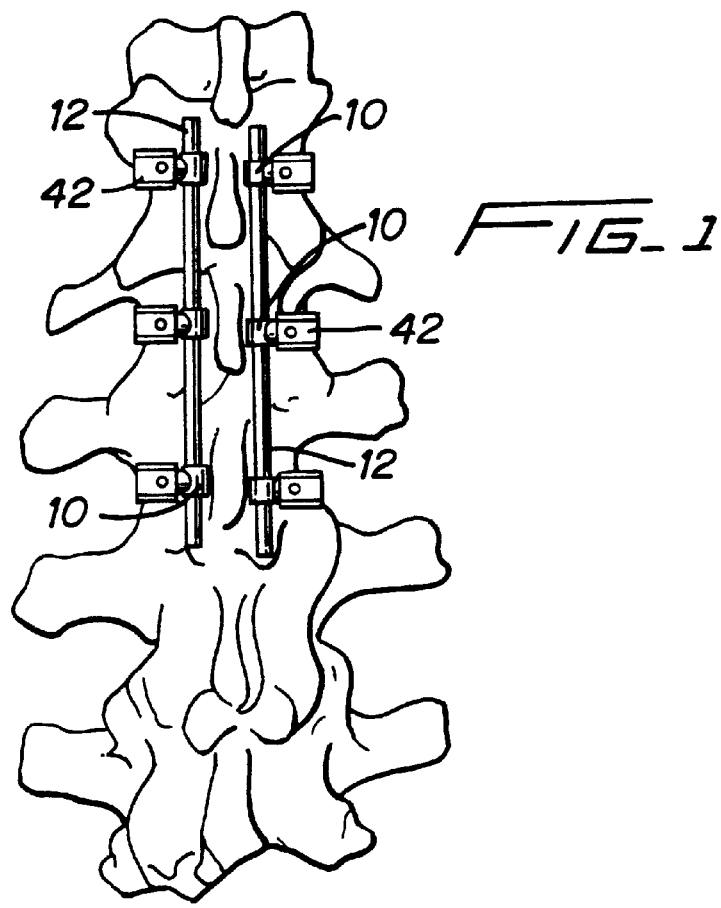
FIG_1
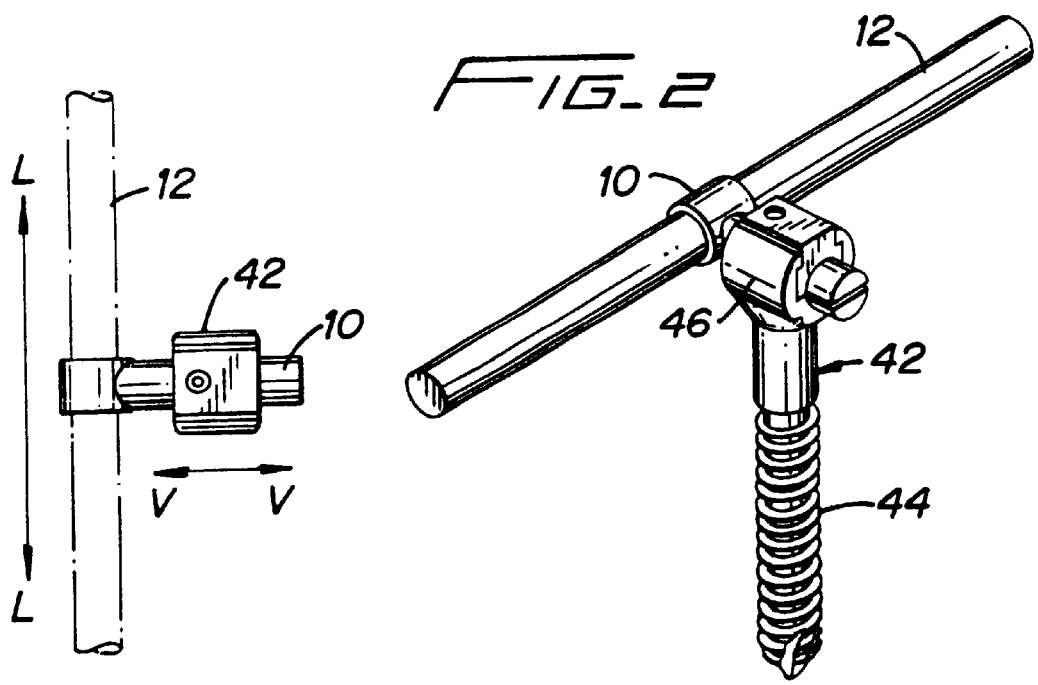
FIG_2
FIG_3

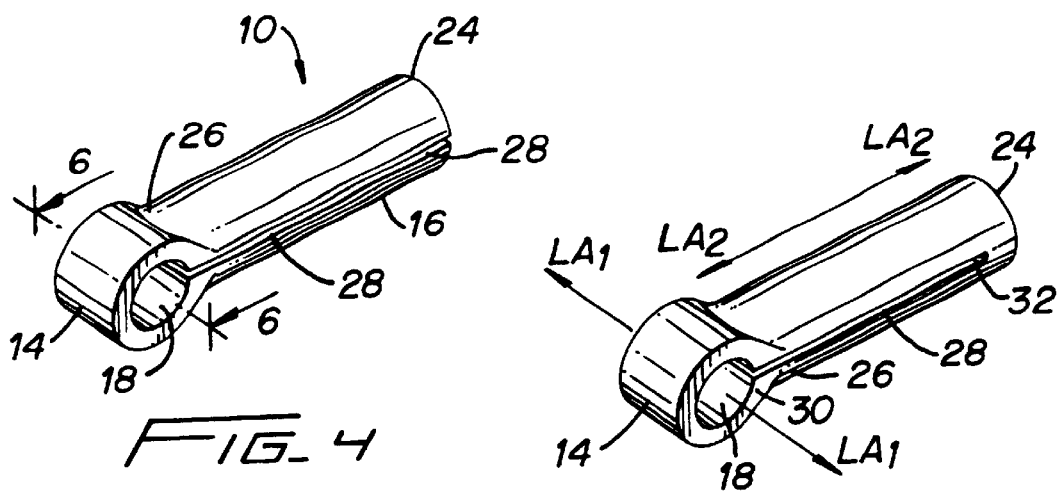
FIG_4
FIG_5
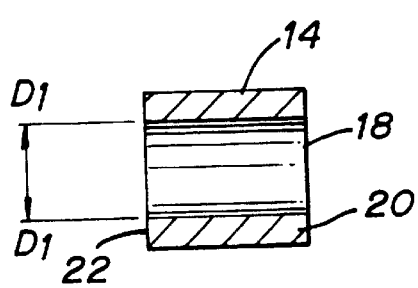
FIG_6A
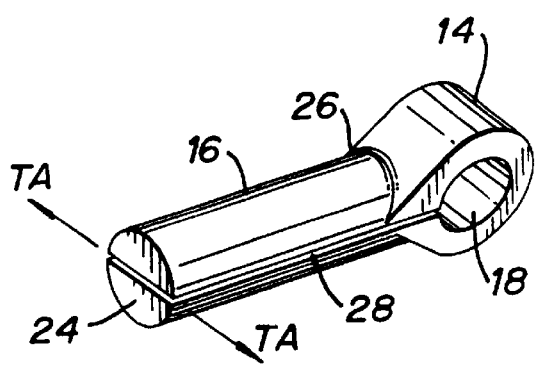
FIG_7
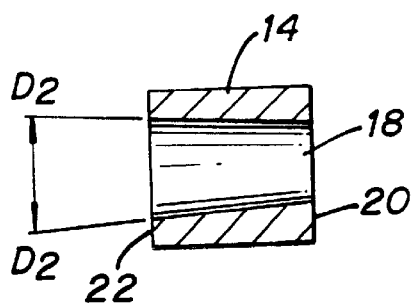
FIG_6B
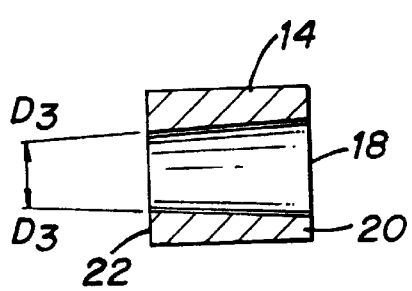
FIG_6C
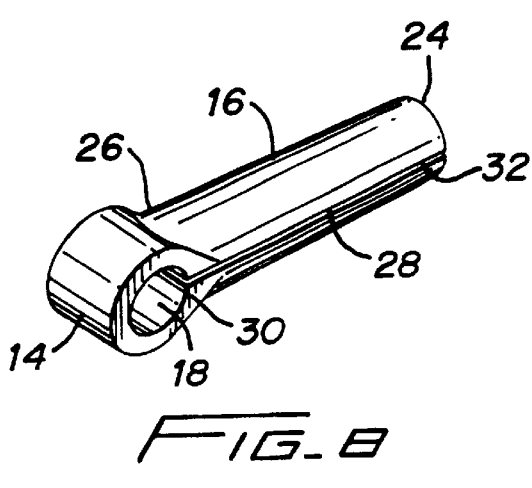
FIG_8

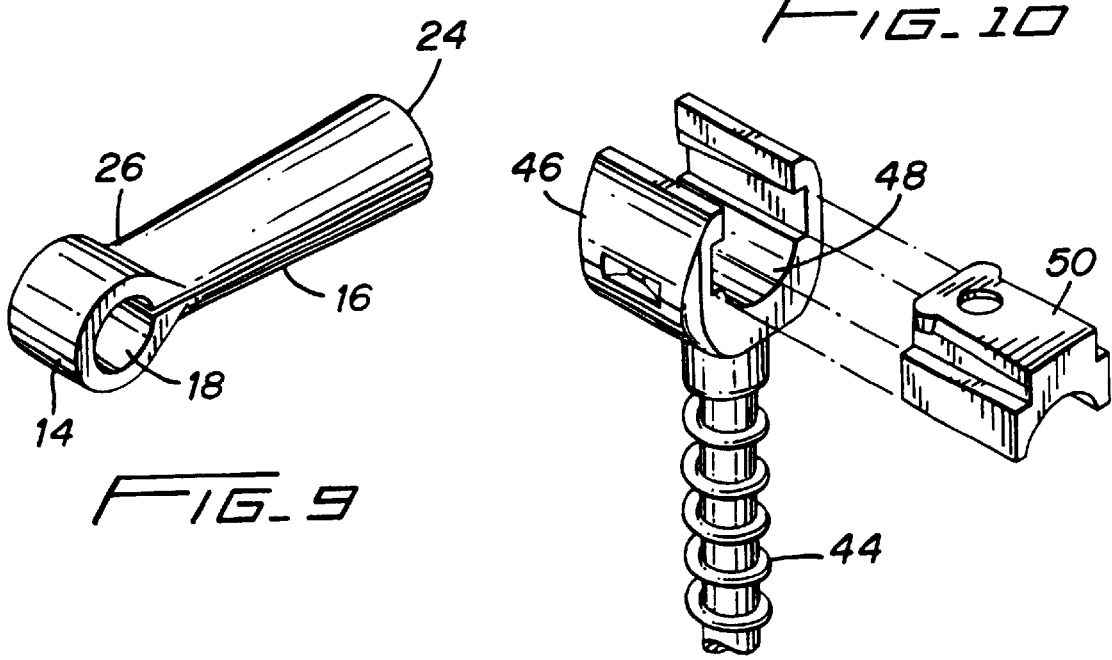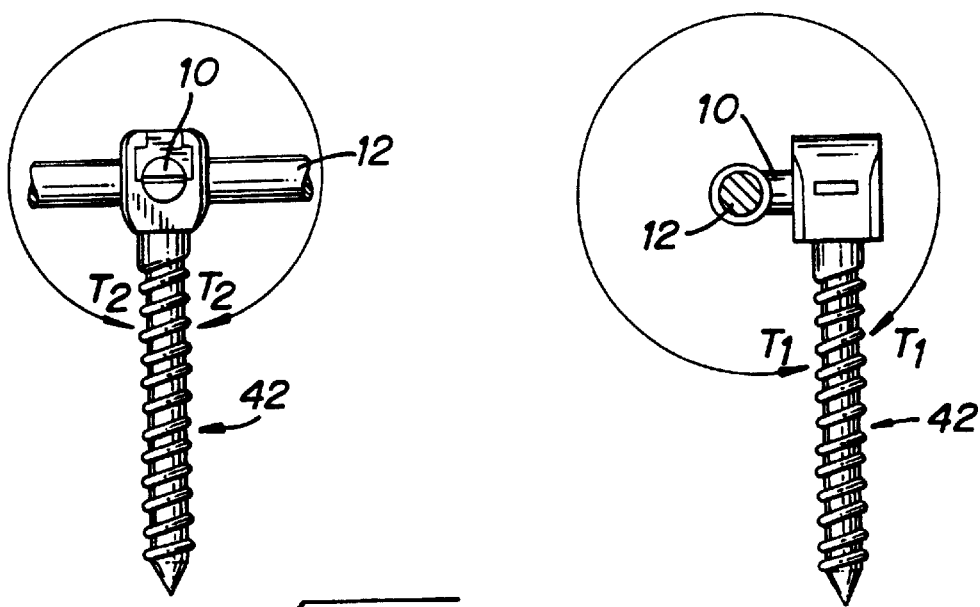

CLAMPING CONNECTOR FOR SPINAL FIXATION SYSTEMS

CROSS-REFERENCE TO RELATED APPLICATIONS

This application is a continuation of U.S. patent application Ser. No. 08/857,137, filed May 15, 1997, now U.S. Pat. No. 6,413,257.

BACKGROUND OF THE INVENTION

1. Field of the Invention

The present invention relates to spinal fixation systems for use in the treatment of spinal deformities and more particularly to a clamping connector for attaching angularly misaligned pedicle screws to transverse spinal rods in spinal fixation systems.

2. Description of the Prior Art

Surgeons treat spinal disorders with spinal fusion augmented with longitudinal spinal rods connected to the spine with lamina hooks or pedicle screws. Such "rod assemblies" generally comprise one or two spinal rods and a plurality of screws inserted through the pedicles and into their respective vertebral bodies. The screws are provided with coupling elements, for coupling the elongate rod to the screws. The rods extends along the longitudinal axis of the spine, coupling to the plurality of screws via their coupling elements. The aligning influence of the rod forces the spine to which it is affixed, to conform to a more proper shape.

Due to anatomical variations, pedicle screws may not properly align with the longitudinal spinal rods. In order to eliminate the need for lateral rod bending, a device is required to connect the rod to the screws in such a way as to compensate for lateral deviation of the spinal rods.

The art contains a variety of attempts at providing instrumentation that permits a range freedom with respect to angulation of the screw and the coupling element. These teachings, however, have generally been complex, and unreliable with respect to durability. The considerable drawbacks associated with the prior art systems include complexity, difficulty properly positioning the rod and the coupling elements, and the tedious manipulation of many small parts associated with the complex spinal fixation devices.

Various connector designs exists to accommodate screws offset from the rod, these include the Smith & Nephew Rogozinski (U.S. Pat. No. 5,102,412) and Finn Systems (U.S. Pat. No. 5,474,551), the Synthes Universal System, and the Zimmer Modulok System (now the Wrightlok System from Wright Medical). Each of these systems require two locking mechanisms for the connector—one to link the pedicle screw to the connector and another to link the connector to the rod. Some of these devices provide variable lateral adjustment while other provide only a fixed distance of offset. The Sofmor Danek TSRH System (U.S. Pat No. 5,282,801) provides a means to offset a screw from the rod with a single set screw yet the lateral distances are fixed.

Other types of screws, hooks and clamps have been used for attaching corrective spinal instrumentation to selected portions of the patient's spine. Examples of pedicle screws and other types of attachments are shown in U.S. Pat. Nos. 5,562,662, 5,498,262, 5,312,404, 5,209,752 and 5,002,542. However, many current bolt to rod connectors constrain the bolt or screw to a predetermined angle in relation to the connector when the assembly is tightened. Tightening the bolt or screw to the connector forces the bolt or screw into a position perpendicular to the connector, creating stresses on the connector and on the bone as the bolt or screw is forced into the perpendicular position.

When spinal rod system are implanted in the sacral region of the spine, the bone screws need to allow for the variability in angulation found between the sacral and lumbar vertebrae. The bone screws also need to be able to pivot in the medial/lateral plane as well as have the ability to pivot and lock in the cephalad/caudal plane while maintaining the proper alignment between an implanted bone screw, a coupler and a rod of a spinal fixation system.

Accordingly, it is a principal object of the present invention to provide a spinal rod linkage apparatus for connecting two or more vertebral bodies in a lateral direction whereby healing of a bone graft between the vertebral bodies is enhanced.

It is another object of the present invention to provide a connector that compensates for angular misalignment, in the transverse plane between both the implanted bolt or screw and the spinal rod, and the bolt or screw and the connector in order to reduce stress on the bolt or screw when it is firmly fastened to the connector.

It is a further object of the present invention to provide a connector that allows for attachment to both the spinal rod and the implanted bone screw with only one locking mechanism.

It is another object of the present invention to provide a connector that provides for variable lateral distances between the spinal rod and the implanted pedicle screw.

SUMMARY OF THE INVENTION

The present invention is directed to a one piece connector for connecting angularly misaligned implanted pedicle screws to longitudinal spinal rods in spinal fixation systems. The one piece connector has a body portion and a leg portion that intersects the body portion at a 90° angle. The body portion includes a bore having an inside diameter and a longitudinal axis, with the longitudinal axis of the bore being positioned perpendicular to the longitudinal axis of the leg portion. The leg portion includes a slot placed through a section of the leg portion, the slot being placed along the transverse axis of the leg portion and parallel to the longitudinal axis of the leg portion. The slot intersects the bore of the body portion perpendicular to the longitudinal axis of the bore. The slot allows the one piece connector to be securely clamped around a longitudinal spinal rod when a pedicle screw is implanted at variable distances from the longitudinal spinal rod. The one piece connector allows for angular misalignment of an implanted pedicle screw in relation to a longitudinal spinal rod and the one piece connector, and for the attachment of the one piece connector to both the longitudinal spinal rod and to the implanted pedicle screw with a single locking mechanism when the one piece connector is used in a spinal fixation system.

BRIEF DESCRIPTION OF THE DRAWINGS

A better understanding of the invention can be obtained when the detailed description of exemplary embodiments set forth below is reviewed in conjunction with the accompanying drawings, in which:

FIG. 1 is a schematic view of a human spine with an implanted spinal fixation system using the connectors of the present invention;

FIG. 2 is a perspective view of a section of a spinal fixation system illustrating the connector of the present invention attaching a pedicle screw to a spinal rod;

FIG. 3 is a top plane view of the assembly of FIG. 2;

FIG. 4 is a perspective view of one embodiment of the present invention;

FIG. 5 is a perspective view of another embodiment of the present invention;

FIG. 6A is a cross-sectional view of the present invention of FIG. 4 taken along lines 6—6 showing the inner surface of the bore;

FIG. 6B is a cross-sectional view of the subject invention of FIG. 4 taken along lines 6—6 showing the bore tapering in a first direction;

FIG. 6C is a cross-sectional view of the present invention of FIG. 4 taken along lines 6—6 showing the inside surface of the bore tapering in a second direction;

FIG. 7 is a perspective view of the first end of the invention of FIG. 4;

FIG. 8 is a perspective of an alternative embodiment of the present invention;

FIG. 9 is a perspective view of a second alternative embodiment of the present invention;

FIG. 10 is a perspective view of a portion of the pedicle screw of FIG. 2 showing a locking mechanism for connecting the present invention to the implanted pedicle screw;

FIG. 11 is a plane view of the present invention of FIG. 2 illustrating a first range of rotation; and FIG. 12 is a side plane view of the present invention of FIG. 2 illustrating a second range of rotation.

DETAILED DESCRIPTION OF INVENTION

The present invention is directed to a one piece connector 10 that is used in spinal fixation systems such as the one shown in FIG. 1. Spinal fixation systems typically include spinal rods 12 and pedicle screws 42 or bone bolts (not shown). The one piece connector 10 includes a body portion 14 and a leg portion 16 (FIGS. 4 and 7). Body portion 14, in a preferred embodiment is generally cylindrical in shape with a longitudinal through bore 18 that has a longitudinal axis LA1—LA1, as shown in FIG. 5. However, body portion 14 can also have other shapes, such as for example, a spherical, oval or cubic shape. Bore 18 has a first end 20 and a second end 22 and an inside diameter D1—D1 (FIG. 6A) that in one embodiment is a constant dimension along the longitudinal axis LA1—LA1 from first end 20 to second end 22. Alternatively bore 18 can taper from a smaller inside diameter at first end 20 to a larger inside diameter D2—D2 at end 22 as shown in FIG. 6B or conversely bore 18 can taper from a larger diameter at end 20 to a smaller inside diameter D3—D3 at second end 22 as illustrated in FIG. 6C. However, in all embodiments, the inside diameter of bore 18 will be greater than an outside diameter of an appropriately sized spinal rod that is part of a spinal fixation system.

Leg portion 16 is generally a solid cylinder with a first end 24 and a second end 26 with the second end 26 intersecting the body portion 14 at a 90° angle (FIG. 7). Leg portion's 16 outer surface can be either smooth or textured. Leg portion 16 has a longitudinal axis LA2—LA2 (FIG. 5) and a transverse axis TA—TA (FIG. 7). Thus, longitudinal axis LA1—LA1 of bore 18 is positioned perpendicular to the longitudinal axis LA2—LA2 of leg portion 16. Leg portion 16 is split in two portions with a narrow slot 28, that is positioned along a transverse axis TA—TA and runs parallel to the longitudinal axis LA2—LA2 of leg portion 16 (FIGS. 4 and 7). Slot 28 includes a first end 30 and a second end 32 with first end 30 intersecting bore 18 of body portion 14 perpendicular to the longitudinal axis LA1—LA1 of bore 18, at the second end 26 of leg portion 16. Slot 28 has a constant width from first end 30 to second end 32 with the width being greater than the difference between the inside diameter of bore 18 and an outside diameter of a selected spinal rod 12. The width of slot 28 creates a clamping force on spinal rod 12 when the one piece connector 10 is placed over spinal rod 12 and connected to an implanted pedicle screw 42. Alternatively, the width of slot 28 can taper from a smaller width at first end 30 to a larger width at second end 32 or conversely from a larger width at first end 30 to a smaller width at second end 32. This tapering of the width of slot 28 increases the clamping force of the one piece connector 10 on spinal rod 12 when pedicle screw 42 is connected to the one piece connector 10 at variable points along the longitudinal axis LA2—LA2 of the leg portion 16. In one embodiment, second end 32 of slot 28 of the one piece connector 10 extends to and creates an opening in the first end 24 of leg portion 16 (FIGS. 4 and 7). In a second embodiment, as shown in FIG. 5, second end 32 of slot 28 stops short of the first end 24 of leg portion 16 so as to create a solid portion at the first end 24 of leg portion 16.

Alternatively, leg portion 16 of the one piece connector can taper from a larger outside diameter at second end 26 to a smaller outside diameter at first end 24 (FIG. 8) or conversely from a larger outside diameter at first end 24 to a smaller outside diameter at second end 26 of leg portion 16 (FIG. 9). The tapering of leg portion 16 also increases the clamping force of the one piece connector 10 on the longitudinal spinal rod 12 when pedicle screw 42 is connected to the one piece connector 10 at variable points along the longitudinal axis LA2—LA2 of the leg portion 16.

As an example only, one size of the one piece connector 10 can have a leg portion 16 with a length of approximately 0.49 inches and a diameter of approximately 0.2 inches, and a body portion 14 with an outside diameter of approximately 0.3 inches and a bore 18 with a diameter of approximately 0.2 inches.

The inside diameter of bore 18 of body portion 14 allows the one piece connector 10 to slide along the longitudinal spinal rod (line L—L in FIG. 3) in order to correctly position the one piece connector in relation to the implanted pedicle screw 42. The inside diameter of bore 18 of body portion 14 also allows for a 360° rotation of the one piece connector 10 around the spinal rod 12 (line T1—T1 in FIG. 11). This rotation allows for any transverse angular misalignment between the implanted pedicle screw 42 and the spinal rod 12 when the one piece connector is secured in place. The ability of the one piece connector to compensate for this angular misalignment reduces stress on the pedicle screw 42 and reduces lateral bending of the spinal rod 12 when the pedicle screw 42 is firmly fastened to the one piece connector 10 and the connector 10 is firmly clamped to spinal rod 12. Additionally, when the one piece connector 10 is attached to the pedicle screw 42, the generally circular shape of leg portion 16 allows the pedicle screw 42 to rotate 360° around leg portion 16 prior to being mechanically locked to the one piece connector 10 (line T2—T2 in FIG. 12). This rotation allows for any transverse angular misalignment between the one piece connector 10 and the implanted pedicle screw 42 when the one piece connector is secured in place. The ability of the one piece connector 10 to compensate for this angular misalignment also reduces stress on the pedicle screw 42 and reduces lateral bending of the spinal rod 12 when the pedicle screw 42 is firmly fastened to the one piece connector 10 and the connector 10 is firmly clamped to spinal rod 12.

The one piece connector 10 also allows the pedicle screw 42 to be offset at variable lateral distances from the spinal rod 12, as shown by line V—V in FIG. 3. The pedicle screw 42 can be locked to the one piece connector 10 at various selected points between the first and second ends 24, 26 of leg portion 16 of the one piece connector 10.

An inventive feature of the one piece connector 10 is its ability to be locked in place on both the longitudinal spinal rod 12 and the implanted pedicle screw 42 with a single locking mechanism on the pedicle screw 42. When used in a spinal fixation system, body portion 14 clamps around spinal rod 12. Pedicle screw 42 typically includes a U-shaped opening, a through bore or some other opening shaped to accommodate the one piece connector 10. Pedicle screw 42 including some form of a locking mechanism for locking the one piece connector 10 or other cylindrical member into the pedicle screw 42. Typical locking mechanisms found on pedicle screws or bone bolts include various kinds of tops or caps that include set screws or taper locking caps or a locking nut for use with bone bolts. These various locking mechanisms are known to one skilled in the art.

An example of a pedicle screw that can be used with the one piece connector is illustrated in FIGS. 2 and 10. Pedicle screw 42 has a shaft portion 44 and a top portion 46 that includes a U-shaped opening 48 configured to receive the one piece connector 10. A locking cap 50 is inserted into the U-shaped opening 48 in order to damp the one piece connector 10 into the pedicle screw 42. When the one piece connectors 10 are used in a spinal fixation system, the spinal rod 12 is placed through bore 18 of the body portion 14 of each connector and the connectors 10 are positioned along the spinal rod 12 in proper alignment with the implanted pedicle screws 42. The one piece connector 10 is angularly adjusted in order to compensate for the pedicle screws 42 that are misaligned in relation to the spinal rod 12. Head 46 of the pedicle screw 42 is positioned so that the U-shaped opening 48 is perpendicular to the longitudinal spinal rod 12. Leg portion 16 of the one piece connector 10 is placed through the U-shaped opening 48 and locking cap 50 is inserted into the U-shaped opening 48 in order to clamp the one piece connector 10 into the pedicle screw 42. As locking cap 50 is locked into place, it compresses the leg portion 16, which causes slot 28 to be compressed which causes body portion 14 of the one piece connector 10 to clamp around the spinal rod 12.

The one piece connector 10, thus provides a secure link between the spinal rod 12 and the implanted pedicle screw 42 with a single connector and a single locking mechanism. The one piece connector 10 allows the pedicle screw 44 to be clamped to the one piece connector at various angles and the one piece connector 10 to be clamped to the spinal rod 12 at various angles.

The foregoing disclosure and description of the invention are illustrative and explanatory thereof, and various changes in the details of the illustrated apparatus and construction and method of operation may be made without departing from the spirit of the invention.

What is claimed is:

1. A device for connecting a pedicle screw to an elongated rod, which comprises:
    a body portion defining an opening having a first dimension to permit passage of the elongated rod and a second dimension for compressively engaging the rod to secure the rod relative to the body portion;
    a leg of circular cross section depending from the body portion, the leg adapted for engagement with the pedicle screw; and
    a locking member rotatably engageable with the leg and movable to cause the body portion to assume the second dimension of the opening thereby securing the rod relative to the body portion.

2. The device according to claim 1 wherein the leg includes the first and second leg portions.

3. The device according to claim 2 wherein the first and second leg portions are movable to an approximated position to cause movement of the body portion to the second dimension of the opening.

4. The device according to claim 3 wherein the locking member is adapted to exert a force on one of the first and second leg portions to move the first and second leg portions to the approximated position.

5. The device according to claim 4 wherein the locking member is adapted to secure a pedicle screw relative to the leg portions and to move the leg portions to approximated position during movement of the locking member to a secured position thereof.

6. The device according to claim 1 wherein the locking member is adapted to cooperate with the leg to secure the pedicle screw relative to the leg upon movement of the locking member to a secured position thereof.

7. The device according to claim 1 wherein the leg is of a length to allow the pedicle screw to be offset at variable lateral distances from the elongated rod.

8. A device for connecting a pedicle screw to an elongated rod, which comprises:
    a body defining an opening for reception of an elongated rod; and
    a pair of legs of circular cross section extending from the body and adapted for engagement with the pedicle screw, the legs being adapted for relative movement from a first position to a second position to reduce a dimension of the opening of the body to thereby cause surfaces of the body to securely engage the elongated rod within the opening.

9. The device according to claim 8 including a locking member engageable with at least one of the legs and movable to cause relative movement of the legs to the second position thereof.

10. The device according to claim 9 wherein the legs are in spaced relation when in the first position thereof and are in approximated relation when in the second position thereof.

11. The device according to claim 10 wherein the locking member is adapted to exert a force on one of the legs to cause relative movement of the legs to the second position thereof.

12. The device according to claim 11 wherein the locking member is adapted to cooperate with the pedicle screw to compress the legs to move the legs to the second position thereof.

13. The device according to claim 9 wherein the leg is of a length to allow the pedicle screw to be offset at variable lateral distances from the elongated rod.

14. A spinal implant system for connection to a spinal rod, which comprises:
    a spinal rod connector including:
        a connector body having an interior portion defining a passage for reception of a spinal rod; and
        a locking member linked to the connector body, the locking member moveable to reduce a dimension of the passage of the connector body to thereby cause the interior portion to securely engage the spinal rod; and
    a pedicle screw mountable to the spinal rod connector.

15. The spinal implant system according to claim 14 wherein the bone screw includes a screw head and a screw extending from the screw head.

16. The spinal implant system according to claim 15 wherein the locking member is operatively engageable with the screw head, the locking member and the screw head being adapted for relative movement to reduce the dimension of the passage of the connector body.

17. The spinal implant system according to claim 15 wherein the spinal rod connector includes a leg extension connected to the connector body, the leg extension adapted to mount the bone screw.

18. The spinal implant system according to claim 17 wherein the leg extension includes the first and second leg portions, the first and second leg portions adapted for relative movement upon movement of the locking member to a secured position thereof to cause the interior portion of the connector body to securely engage the spinal rod.

19. The spinal implant system according to claim 18 wherein the locking member is positioned to engage the first leg portion and the screw head is positioned to engage the second leg portion, whereby upon movement of the locking member to the secured position thereof, the locking member and the screw head cooperate to compress the first and second leg portions to cause movement of the first and second leg portions to a relative approximated position thereof.

20. The device according to claim 19 wherein the locking member is adapted to secure the pedicle screw relative to the leg portions and to move the leg portions to the approximated position during movement of the locking member to the secured position thereof.

21. The spinal implant system according to claim 17 wherein the locking member is adapted to exert a force substantially parallel to an axis of the screw shaft upon movement of the locking member to a secured position thereof.

* * * * *